United States Patent [19]

Grady

[11] Patent Number: 5,084,011
[45] Date of Patent: Jan. 28, 1992

[54] METHOD FOR OXYGEN THERAPY USING HYPERBARICALLY OXYGENATED LIQUID

[76] Inventor: Daniel J. Grady, 305 Yadkin Rd., Southern Pines, N.C. 28387

[21] Appl. No.: 470,342
[22] Filed: Jan. 25, 1990
[51] Int. Cl.$^5$ .............................................. A61K 31/00
[52] U.S. Cl. ......................................... 604/24; 604/4; 604/49; 604/52
[58] Field of Search ........................ 604/4–6, 604/23–29, 49–53; 128/DIG. 3, 898; 422/44–48

[56] References Cited

U.S. PATENT DOCUMENTS

| | | | |
|---|---|---|---|
| 4,445,500 | 5/1984 | Osterholm | 128/898 X |
| 4,657,532 | 4/1987 | Osterholm | 604/24 |
| 4,919,895 | 4/1990 | Heldebrant | 128/DIG. 3 X |
| 4,923,442 | 5/1990 | Segall et al. | 604/52 |
| 4,963,130 | 10/1990 | Osterholm | 604/24 |

Primary Examiner—Robert A. Hafer
Assistant Examiner—Kerry Owens
Attorney, Agent, or Firm—Rhodes, Coats & Bennett

[57] ABSTRACT

This invention is a method of preparing and utilizing oxygenated liquids for medical and therapeutic purposes. Non-blood liquid solutions are oxygenated using a gas liquid contact apparatus. Conditions of increased ambient pressure and decreased temperature are created to maximally dissolve gaseous oxygen into liquids. In addition, an electromagnetic stirring is used to homogeneously mix the gaseous oxygen and liquid. Following the oxygenation of the liquid is anaerobically procured from the gas liquid contact apparatus in order to maintain high dissolved oxygen partial pressures in the liquid. The oxygenated liquid may be intravenously injected to titrate blood oxygen levels, or the oxygenated liquid may be systemically administered for absorption into tissues and the bloodstream.

23 Claims, 9 Drawing Sheets

METHOD FOR OXYGEN THERAPY USING HYPERBARICALLY OXYGENATED LIQUID

FIELD OF THE INVENTION

This invention relates to medical methods and processes. More specifically, this invention relates to the injection of oxygenated liquids into the bloodstream and applied to body surfaces and cavities as a form of oxygen therapy.

BACKGROUND OF INVENTION

Tissue hypoxia, or a deficiency of molecular oxygen available for cellular metabolism, is a common cause of death in critically ill people. Tissue hypoxia is caused by innumerable heart and lung diseases and is frequently associated with impaired oxygen delivery to cells and tissues. Within the past century, numerous methods have been developed to attempt to improve oxygen delivery to tissues.

One method of improving oxygen delivery to tissues is through the inhalation of gaseous oxygen through normal respiratory channels. To date, gaseous oxygen may be inhaled through numerous devices such as masks, tents, cannulas, catheters, hoods, and mechanical ventilator systems. In essence, the purpose of oxygen inhalation is to increase the quantity of oxygen absorbed into the blood in hopes of improving oxygen delivery to cells and tissues. However, as a method of oxygen therapy, the inhalation of gaseous oxygen is associated with several complications and limitations. First, if the breathing passages are blocked or if a person has stopped breathing altogether, inadequate amounts of oxygen are absorbed into the bloodstream to sustain cellular metabolism. Second, gaseous oxygen inhalation may be toxic to tissues if inhaled in high concentrations over prolonged periods. Third, the inhalation of high concentrations of gaseous oxygen causes atelectasis or lung collapse.

Other complex methods and processes have been developed to improve oxygen delivery to tissues. These include hyperbaric breathing chambers, extra-corporeal membrane oxygenation (ECMO) or heart-lung bypass machines, intravenous injection of gaseous oxygen, and fluid breathing.

Hyperbaric breathing chambers involve the placement of a person inside a sealed chamber with the subsequent pressurization of the chamber. During chamber pressurization, the patient inhales gaseous oxygen through normal respiratory channels which results in increased blood oxygen levels. However, multiple limitations exist for this method of oxygen therapy. First, the breathing chambers are extremely expensive. Second, complex facilities and highly trained personnel are needed for safe operation. Third, once a person is inside a pressurized chamber, medical personnel outside of the chamber do not have access to the patient. Fourth, since the patient's body is placed inside the chamber, the amount of pressure utilized to pressurize the chamber is limited. Fifth, following chamber pressurization, prolonged time periods are required for the de-pressurization process. Last, the increased blood oxygen levels achieved during chamber pressurization and oxygen inhalation are lost when the chamber is de-pressurized and the person is removed from the chamber. Numerous complications have been documented with this method of oxygen therapy including fires, explosions, oxygen toxicity, gas embolism, and Caisson's disease from rapid chamber de-pressurization.

Another method of oxygen therapy, extra-corporeal membrane oxygenation, involves the removal of the blood from the body, exposing the blood to gaseous oxygen by an oxygenator apparatus, and reintroducing the blood into the body. The limitations of this method for improving oxygenation are obvious when one considers the potential complications associated with removal of blood from the body. First, blood catheters must be surgically inserted within major blood vessels. Second, accidental exsanguination or blood loss, infection, and damage to blood cells are documented complications. Last, this method requires highly trained personnel and is extremely expensive.

Another method of delivering oxygen to tissues which has been tried is intravenous injection of gaseous oxygen. This method has been found to be extremely hazardous. Gas bubbles tend to coalesce in the veins and occlude smaller pulmonary arteries. The resulting gaseous pulmonary embolism causes a decreased pulmonary circulation, arterial hypoxemia, and systemic hypoxia. Due to the extreme hazards, this method of oxygen therapy is generally considered to have little, if any, practical utility.

A relatively new method of oxygen therapy involves fluid breathing. The method was first described by Klystra (1958) who submerged both mice and dogs in a salt water solution inside a hyperbaric breathing chamber. Following pressurization of the chamber with oxygen, the animals inhaled the liquid through normal respiratory channels. The animals remained alive for varying time periods while breathing the liquid solution. Several complications of fluid breathing were noted including increased work of breathing, deficient carbon dioxide excretion, increased fluid retention within the lungs, and grossly impaired respiratory function following the transition from fluid to air breathing.

More recently, fluid breathing by a human infant was reported in 1989 at Hahnemenn Hospital in Pennsylvania. The infant breathed a fluorocarbon liquid which was oxygenated with pure oxygen gas at ambient barometric pressure. The fluorocarbon mixture was used because of high oxygen solubility in the liquid at normal atmospheric pressures. However, liquid ventilation is associated with several complications including decreased blood oxygen levels (hypoxemia), bronchiolar inflammation, wheezing, and carbon dioxide retention. It should be noted that the infant died after several hours of fluid breathing.

SUMMARY AND OBJECTS OF THE INVENTION

Figure 1:
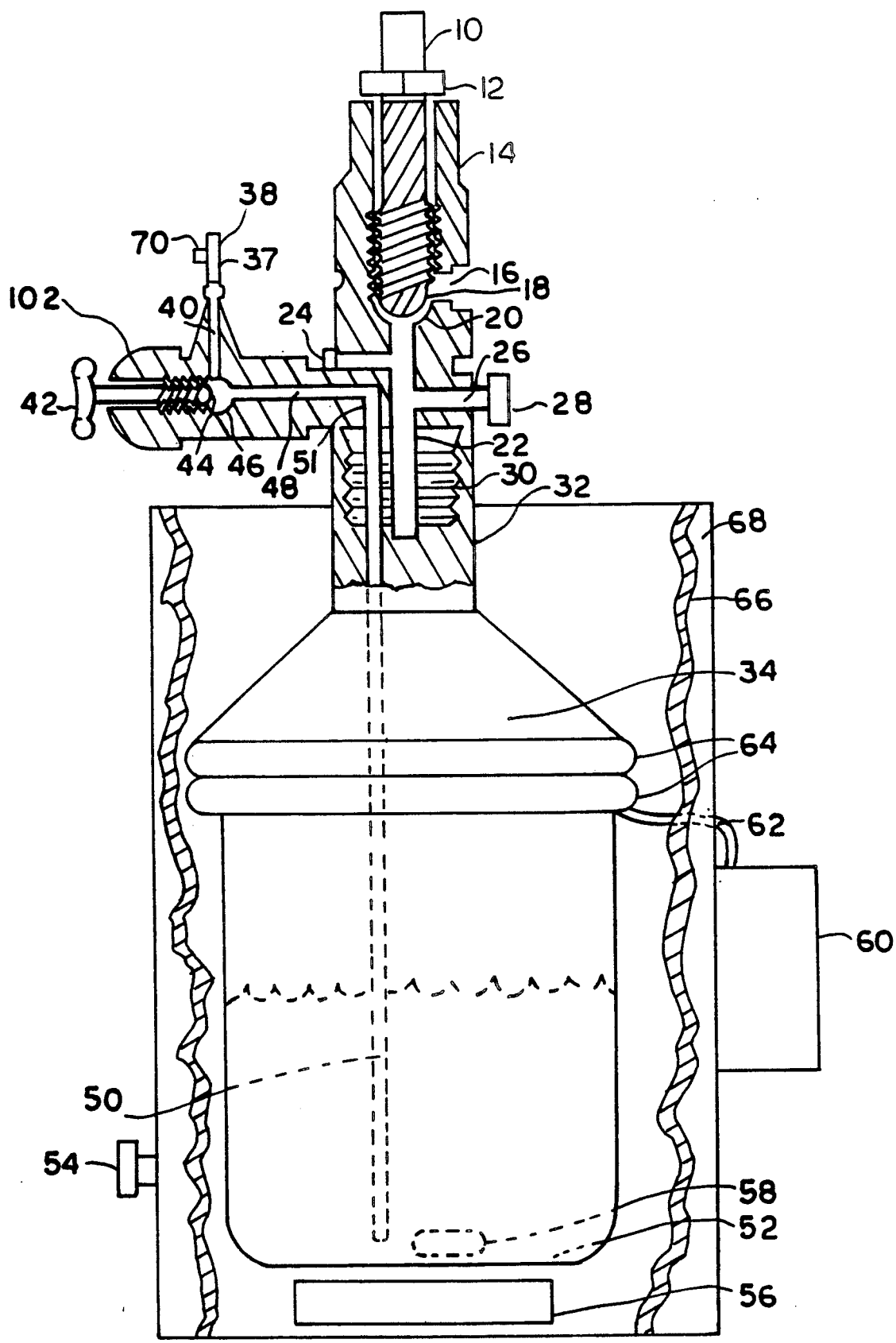
FIG. 1 shows a cross-sectional view of the gas liquid contact apparatus.
Figure 2:
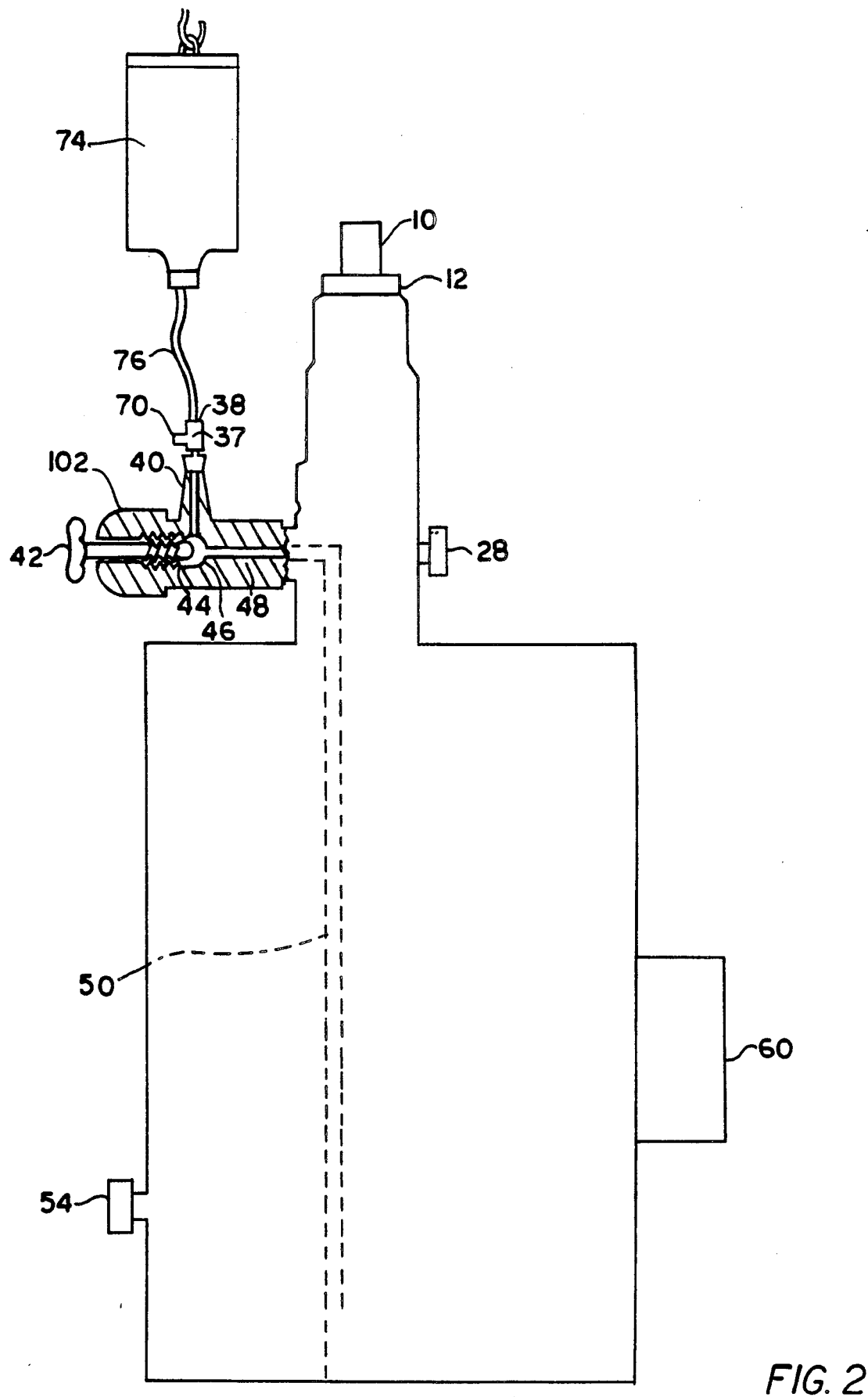
FIG. 2 shows infusion of a sterilized liquid into the gas liquid contact apparatus.
Figure 3:
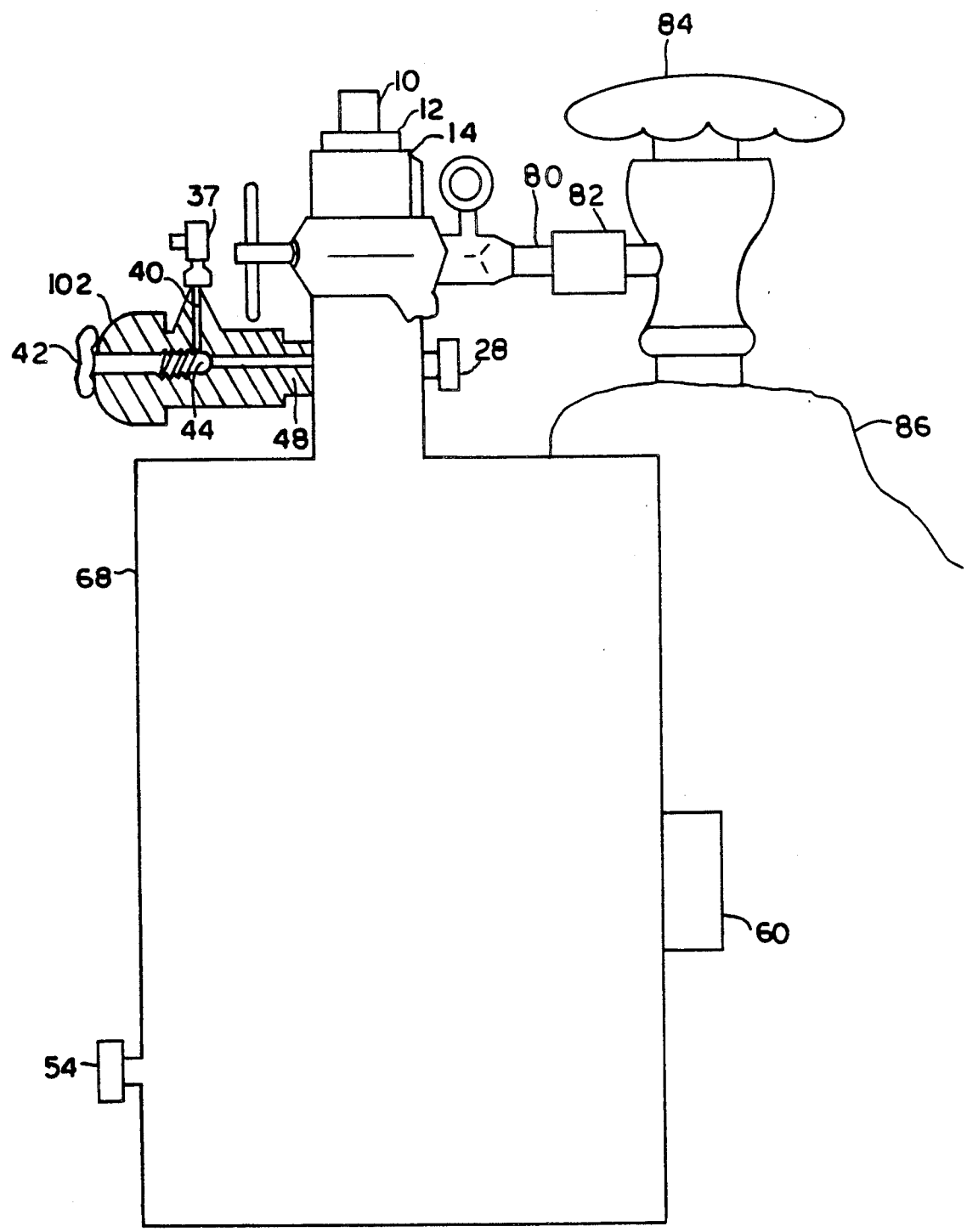
FIG. 3 shows connection of the gas liquid contact apparatus to a cylinder of gaseous oxygen for pressurization of the vessel.

The present invention is a method for delivering oxygen to body tissues which avoids some of the complications associated with prior methods. Briefly, the method involves contacting a liquid with oxygen or oxygen containing gas outside the body under hyperbaric conditions to affect dissolution of oxygen into the liquid. In the preferred embodiment, increased pressures and reduced temperatures are used to increase the saturation level of the liquid. The oxygenated liquid can then be injected intravenously to titrate blood levels. Alternatively, the oxygenated liquid can be systemically administered for absorption into body tissues.

Accordingly, it is a primary object of the present invention to provide a new method of oxygen therapy which is relatively safe and avoids hazards and complications associated with prior methods.

Another object of the present invention is to provide a method of oxygen therapy in which therapeutic liquids oxygenated under hyperbaric conditions are administered to body tissues.

Another object of the present invention is to provide a method of oxygen therapy which is suitable for emergencies such as cardiac arrest and respiratory arrest.

Another object of the present invention is to provide a method of oxygen therapy which avoids complications of gaseous oxygen breathing such as atelectasis and refractory hypoxemia.

Still another object of the present invention is to provide a method of oxygen therapy which avoids complications of hyperbaric breathing chambers such as barotrauma, and Caisson's disease.

Another object of the present invention is to provide a method of oxygen therapy which avoids complications of extracorporeal membrane oxygenation such as infection and exsanguination.

Another object of the present invention is to provide a method of oxygen therapy in which oxygenated liquids may be intravenously injected into the body for absorption into the bloodstream.

Another object of the present invention is to provide a method of oxygen therapy in which oxygenated liquids may be applied systemically to body tissues to improve regional tissue oxygenation.

Still another object of the present invention is to provide a method of oxygen therapy which is relatively easy to employ.

Still another object of the present invention is to provide a method of oxygen therapy which is less expensive than prior methods.

Still another object of the present invention is to provide a gas liquid contact apparatus for oxygenating a liquid externally of the body.

Other objects and advantages of the present invention will become apparent and obvious from a study of the following description and the accompanying drawings which are merely illustrative of such invention.

DETAILED DESCRIPTION OF THE INVENTION

The present invention presents an alternative method for oxygen therapy not previously known. Essentially, the method involves the steps of (1) oxygenating a therapeutic liquid extracorporeally under hyperbaric conditions; and (2) delivering the oxygenated liquid to the patient. Numerous possibilities for delivering the oxygenated liquid exist. For example, the oxygenated liquid can be intravenously injected into the patient's bloodstream, or it can be applied systemically and absorbed through body tissues.

A gas/liquid contact apparatus is employed for oxygenating the liquid. The gas/liquid contact apparatus is shown in FIGS. 1–4. The gas/liquid contact apparatus includes a pressure vessel 34 made of high carbon steel, heat treated steel, manganese steel, nickel or aluminum. The inner lining of the pressure vessel 34, which will directly contact liquid solution, consists of a rust-resistant, non-corrosive substance which is non-reactive with oxygen. Aluminum is a suitable lining material.

Connected to the neck 32 of the pressure vessel 34 is a vessel post 14. The vessel post 14 includes a threaded end 30 which screws into the neck 32 of the pressure vessel 34. A liquid infusion assembly 102 is steel-welded to the vessel post 14 and extends perpendicularly therefrom. Alternatively, the liquid infusion apparatus may be constructed similarly to a standard regulator and attached to the vessel post 14 by a yoke and t-screw (not shown). All joints and connections in the tubing should be made by welding or by use of flanged, threaded slip, or compressed fittings and should be suitable for use with high-pressure oxygen.

A gas valve assembly is contained in the vessel post 14. The gas valve assembly includes a valve stem 10 which is threaded into the vessel post 14. A retaining nut 12 threads onto the valve stem 10 and can be tightened against the top of the vessel post 14 to lock the valve stem 10 in a fixed position. The lower end of the valve stem 10 is rounded to form a direct acting gas valve 18 which is adapted to seat against a valve seat 20. A gas channel 22 extends from the valve seat 20 and communicates with the interior of the pressure vessel 34. A vent passage extends perpendicularly from the gas channel 22 and terminates in a pressure relief valve 24. A gauge passage 26 also extends perpendicularly from the gas channel 22 and connects to a manometer 28.

To open the gas valve, the valve stem 10 can be rotated counterclockwise to unseat the direct acting gas valve 18 from the valve seat 20. When the direct acting valve 18 is unseated, the gas channel 22 communicates with an inlet/outlet port 16 formed in the side of the vessel post 14. To shut off the gas valve, the valve stem is threaded clockwise to reseat the valve 18 against the valve seat 20.

The liquid infusion assembly includes a liquid valve assembly similar to the gas valve assembly. The liquid valve assembly includes a direct acting valve 44 threaded into the liquid infusion assembly. A handle 42 is formed on the outermost end of the direct acting valve. The innermost end of the valve 44 is adapted to seat against a valve seat 46 to shut off the liquid valve. To open the valve, the handle 42 is turned counterclockwise to unseat the valve 44 from the valve seat 46 and establish fluid communication between an inlet channel 40 and liquid channel 48. To shut off the valve, the handle 42 is turned clockwise to reseat the valve 44 against the valve seat 46.

The inlet channel 40 connects to a three position stopcock valve 37 having a standard inlet connector 38 and a luer lock connector 70. The liquid channel 48 is connected by an elbow 51 to a feed tube which extends to the bottom of the pressure vessel 34.

The assembled vessel post 14, pressure vessel 34 and liquid infusion assembly must be capable of withstanding internal gas pressure of at least 3,000 psi without leaks when the vessel contains liquids filled to 50% of its internal volume. The assembled gas liquid contact apparatus shall meet or exceed all relevant requirements of the American Society of Mechanical Engineers (ASME) Boiler and Pressure Vessel Codes. In addition, the fully assembled gas liquid contact apparatus must be capable of withstanding hydrostatic testing to 1.5 times the desired maximum filling pressure of 2,000 psi. All components which come into direct contact with the liquid and/or gas should be made of a rust-resistant, non-corrosive substance which is non-reactive with oxygen.

In the preferred mode of practice, the pressure vessel 34 is refrigerated to approximately 4° celsius. A refrigeration unit 60 containing compressor, condenser, temperature control, and thermostat connects to refrigeration coils 64 which surround the outer surface of the pressure vessel 34. A proximal temperature sensor 62 attaches to the outer surface of the pressure vessel 34. A layer of insulation material 66 encloses the pressure vessel 34 and refrigeration coil 64. Metal casing 68 encloses the insulation 66, the pressure vessel 34 and refrigeration coil 64.

Also, in the preferred mode of practice an electromagnetic stirring apparatus 56 is used to agitate the liquid. The stirring apparatus includes a bead 58 contained within pressure vessel 34 which is moved about by magnetic forces.

The gas liquid contact apparatus is used to oxygenate a liquid which is being used to provide oxygen therapy. The steps employed in the present invention consist of 1) preliminary preparation of the liquid; 2) liquid infusion into the pressure vessel; 3) pressurization of the vessel; 4) mixing of the gas and liquid; 5) removal of the liquid; and 6) administering the oxygenated liquid to the patient.

Prior to infusing a sterilized liquid into the pressure vessel 34, the liquid should have all dissolved gases removed by boiling or other chemical means to prevent the inadvertent compression of gases such as nitrogen. Following the removal of these gases, pure oxygen gas is bubbled through the solution for 30 minutes. After bubbling the oxygen through the liquid, the liquid is maintained in a diffusion-resistant container which prevents contact with air.

Once the liquid is prepared, a container 74 filled with the liquid is connected to the liquid inlet connector 38 of the stopcock valve 37 by means of standard intravenous tubing 76. (See FIG. 2) A standard gas cylinder refilling adapter 80 is connected to the gas inlet/outlet opening 16. Negative subatmospheric pressure is applied to the open end of the refilling adapter 80 by connection to standard suction tubing (not shown). The gas inlet valve stem 10 is opened to allow the suction pressure to be applied to the inside of the pressure vessel 34. The valve handle 42 is rotated counterclockwise to allow the negative subatmospheric pressure inside the pressure vessel 34 to draw the sterilized liquid through the liquid inlet channel 40, past the valve 44 and valve seat 46, through the liquid channel tube 48, and through the feed tube 50. The liquid flows to the floor of the pressure vessel 52. When the pressure vessel 34 is half filled, as indicated by the liquid level gauge 54, the valve handle 42 is rotated to firmly close the valve 44 against the valve seat 46. The suctioning device is then disconnected from the refilling adapter 80.

After the container is filled with sterilized liquid the gas liquid contact apparatus is connected to a large gas cylinder of oxygen 86 by connecting the refill adapter 80 to the gas outlet 82 of the large gas cylinder 86. (See FIG. 3) In other words, the refill adapter 80 connects the gas outlet of the large gas cylinder 86 to the gas inlet/outlet 16 of the gas liquid contact apparatus. The gas inlet valve stem 10 is rotated to open the valve 18 to let oxygen into the pressure vessel 34. The gas liquid contact apparatus is internally pressurized when the large cylinder valve 84 is slowly opened. It is very important to slowly open the large gas cylinder valve to avoid the excessive adiabatic heat of gas compression. The gas liquid contact apparatus may be slowly pressurized to the desired hyperbaric pressure in 100 psi increments by referring to the pressure measured on the gas manometer gauge 28. After the desired pressure is achieved, the large gas cylinder valve 84 is rotated to a closed position, and the gas inlet valve stem 10 is also rotated to a closed position. The refilling adapter 80 may be removed from the gas liquid contact apparatus.

Following the pressurization of the vessel containing the sterilized liquid, the dissolving process of gas into the liquid is further enhanced by activation of the electromagnetic stirring apparatus 56 and magnetic stirring bead 58. The magnetic field generated by the stirring apparatus is believed to increase solubility of the oxygen gas into the liquid because of the affinity of oxygen molecules for the magnetic field. The refrigeration unit 60 can be activated to decrease the temperature of the gas and liquid solution to approximately 4° centigrade. Following activation of the refrigeration unit 60, the refrigerant circulates through the refrigeration coils 64 thereby removing heat from the pressure vessel until the proximal temperature sensor 62 detects the desired temperature. By decreasing the temperature of the solution, the solubility of oxygen increases. Also, the size of the gas bubbles contained in the liquid decreases to a size sufficient to avoid pulmonary embolism when the liquid is injected into the bloodstream. An additional benefit derived from refrigeration is that an increase is realized in the percentage of oxyhemoglobin formed when the liquid is injected into the bloodstream. This additional benefit will be described in more detail in subsequent portions of the specification.

The liquid is maintained in the pressure vessel 34 sufficient time so that the partial pressure of oxygen in the liquid is increased to greater than 159 mm Hg, which is the partial pressure of a liquid under normal atmospheric conditions. It would be more preferable to raise the partial pressure of oxygen in the liquid to above 760 mm Hg, which is the maximum partial pressure of oxygen in liquid subject to a pure oxygen environment under normal atmospheric pressures. However, for best results it is desirable to raise the partial pressure of oxygen in the liquid to at least 2280 to 3040 mm Hg. To obtain these values, the pressure inside pressure vessel 34 will have to be maintained at a minimum of between 3 and 4 atmospheres.

The oxygenated liquid may be used in a variety of ways to treat a patient. To use the oxygenated liquid, it must be drawn from the pressure vessel 34, preferably into a non-diffusable treatment apparatus, which may for instance, be a glass syringe.

Perhaps the most significant method of treatment is through intravenous injection of the liquid into a patient's bloodstream when a lung impairment exists in order to titrate blood oxygen levels.

In blood, oxygen is transported in two forms: (1) physically dissolved in the blood plasma and (2) chemically combined with the hemoglobin contained within red blood cells. The oxygen physically dissolved in blood plasma consists of free oxygen molecules which exert a measurable partial pressure (abbreviated as $po_2$). Significant differences normally exist between the $po_2$ of mixed venous blood (blood traveling towards the lungs to obtain oxygen) and arterial blood (oxygenated blood traveling away from the lungs for distribution throughout the body). In healthy adults with normal cardiopulmonary function, the mixed venous $po_2$ is approximately 40.0 mm Hg. and the arterial $po_2$ is approximately 100.0 mm Hg. Therefore, a primary function of healthy lungs is to allow significant oxygen exchange between inhaled air and blood such that the $po_2$ continuously increases from 40.0 mm Hg. to 100.0 mm Hg. as mixed venous blood traverses the lungs and becomes arterialized.

The second and most substantial way in which oxygen is transported by blood and delivered to tissue is in the form of oxyhemoglobin. The formation of oxyhemoglobin occurs inside the red blood cells as hemoglobin chemically combines with oxygen molecules. Since the red blood cells remain submerged in the watery plasma, the partial pressure of oxygen dissolved in the plasma ($po_2$) is extremely important because of its effect on the formation of oxyhemoglobin. In essence, the plasma $po_2$ establishes the pressure gradient which causes free oxygen molecules in the plasma to diffuse inside the red blood cell in the formation of oxyhemoglobin. The hemoglobin per cent saturation measurement refers to the percentage of hemoglobin bond sites which exist as oxyhemoglobin. In healthy adults, the normal mixed venous hemoglobin saturation is about 75% at a $po_2$ of 40.0 mm Hg. Following oxygen absorption into the blood at the lungs, the arterial hemoglobin saturation is about 97% at a $po_2$ of 100.0 mm Hg.

The chemical bond between hemoglobin and oxygen in the formation of oxyhemoglobin is affected by multiple factors. These factors include blood pH, temperature, dissolved carbon dioxide concentration, and 2,3 diphosphoglycerate concentration. The nature of this bond is such that, in mixed venous blood with a $po_2$ of 40.0 mm Hg., a small increase in the $po_2$ results in a large increase in hemoglobin saturation.

The injection of a super-oxygenated liquid into mixed venous blood is intended to result in an increased $po_2$ and hemoglobin saturation as the liquid continuously mixes with the blood plasma and red blood cells. In addition, because of the effect of temperature on the chemical affinity between hemoglobin and oxygen, the injection of a relatively cold intravenous liquid at approximately 4.0 degrees centigrade will enhance the formation of oxyhemoglobin because of increased chemical bonding affinity between hemoglobin and oxygen.

The total oxygen content of blood is determined by adding the (1) dissolved oxygen with (2) the oxygen chemically combined with hemoglobin. By convention, total oxygen content of blood is expressed in the form of the number of milliliters of oxygen contained in each 100.0 milliliters of blood or volumes per cent (abbreviated as vol. %). In mixed venous blood, the oxygen content is approximately 15 volumes per cent (15 vol. %). Arterial blood has an oxygen content of approximately 20.4 vol. %.

Oxygen delivery, which refers to the amount of oxygen delivered to body tissues each minute, may be determined by multiplying the arterial oxygen content by the cardiac output and a factor of 10. The normal amount of oxygen delivered to tissues throughout the body is approximately 800.0 to 1000.0 milliliters of oxygen per minute. A summary of normal values for the process of blood oxygenation may be found in Table 1.

TABLE 1

| Normal Values in Blood Oxygenation | | |
|---|---|---|
| | Mixed Venous Blood | Arterial Blood |
| $po_2$ (mm Hg.) | 40.0 | 100.0 |
| $HbO_2$ percent saturation | 75% | 97% |
| Oxygen Content (vol. %) | 15 vol. % | 20 vol. % |
| Normal Oxygen Delivery to Tissues Per Minute: | 800–1000 ml. | |

These values are found in normal, healthy adults. During lung disease, the values may substantially decrease.

Therefore, the primary purpose of intravenously injecting a super-oxygenated liquid into the bloodstream is to maintain adequate oxygen delivery to tissues especially when lung impairment exists. When a super-oxygenated liquid is intravenously injected into the bloodstream, the goal is to increase the mixed venous blood oxygen content to levels which will maintain adequate oxygen delivery to tissues. Basically, this method may be used to either supplement or replace the oxygenation function of the lungs when the normal lung function is impaired by disease.

Figure 4:
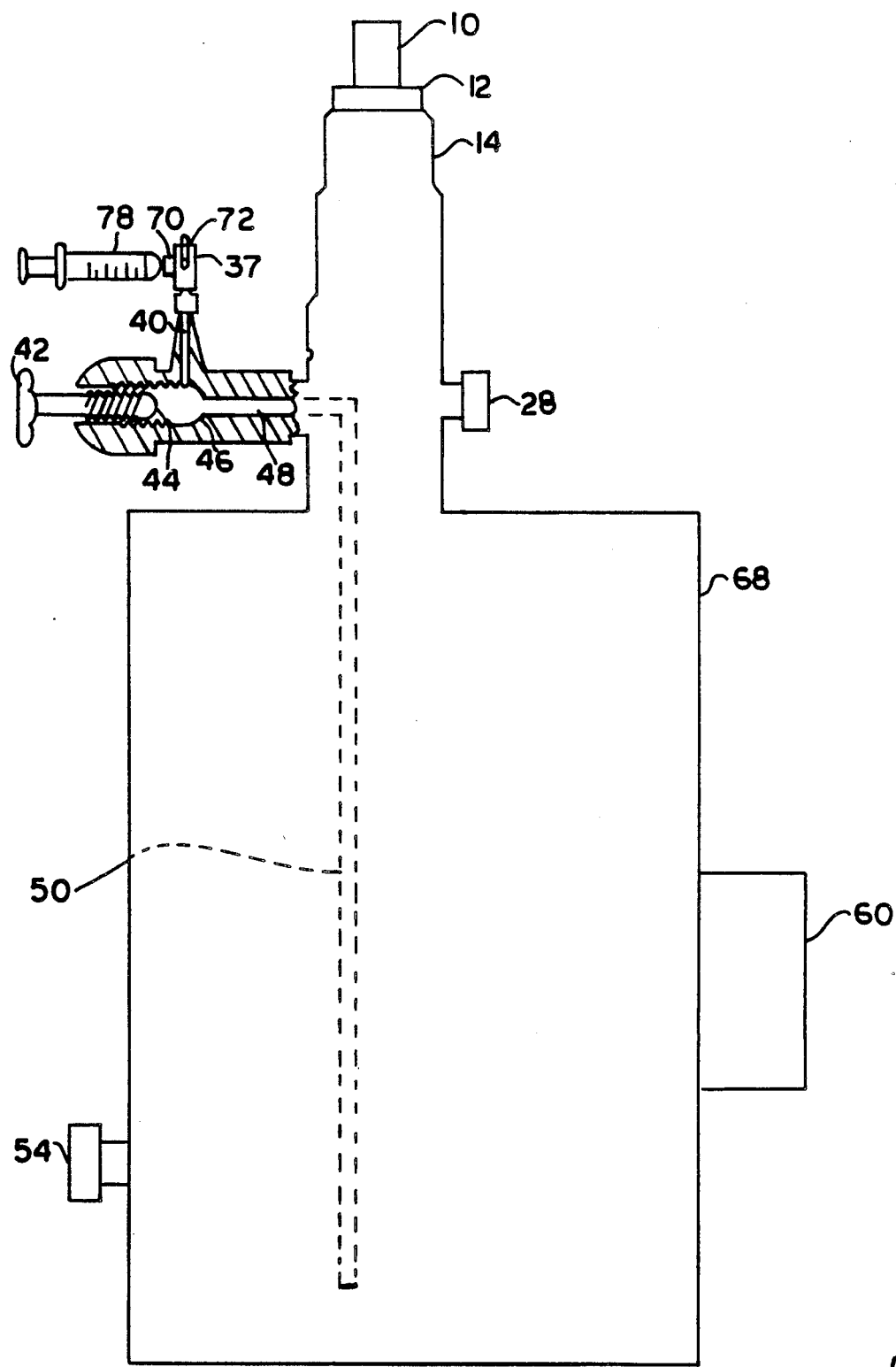
FIG. 4 shows withdrawal of the oxygenated liquid from the pressurized vessel using a glass syringe.

To inject the oxygenated liquid a glass syringe should be used. As shown in FIG. 4 a glass syringe 78 (50 or 100 ml.) is connected to the luer lock syringe connection 70. The stopcock valve 37 is rotated to allow the oxygenated liquid to enter the syringe after the valve handle 42 is rotated to move the valve 44 away from the valve seat 46. The pressure inside the pressure vessel 34 above the surface of the liquid forces the liquid to flow up the feed tube 50, past the liquid channel 48, and up into the inlet channel 40. After the liquid reaches the stopcock valve 37, the liquid may be anaerobically drawn into the glass syringe 78, so that the partial pressure of oxygen in the liquid is maintained at the desired level. After drawing the liquid into the glass syringe 78, the valve handle 42 is rotated to close the valve 44 against the valve seat 46, thereby stopping the liquid flow. In addition, the stopcock valve handle 72 is rotated to close the stopcock valve 37 following removal of the syringe.

Figure 5:
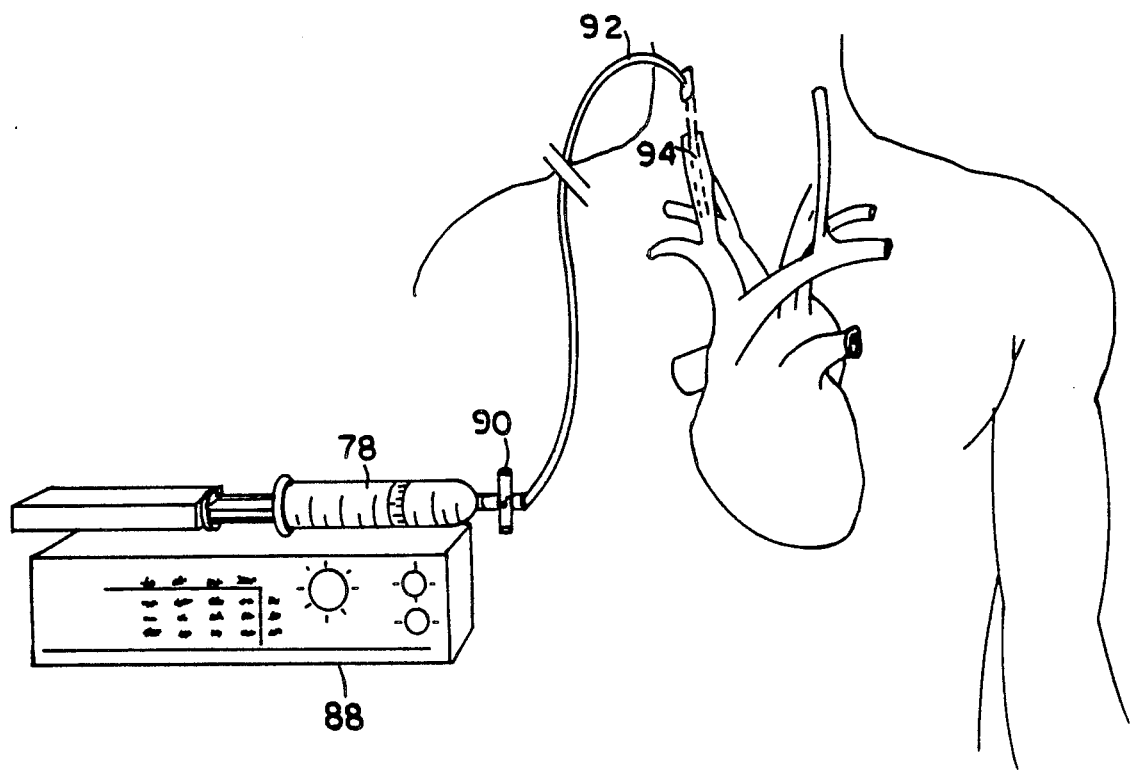
FIG. 5 shows intravenous injection of the oxygenated liquid through diffusion-resistant tubing using a controlled infusion pump.
Figure 6:
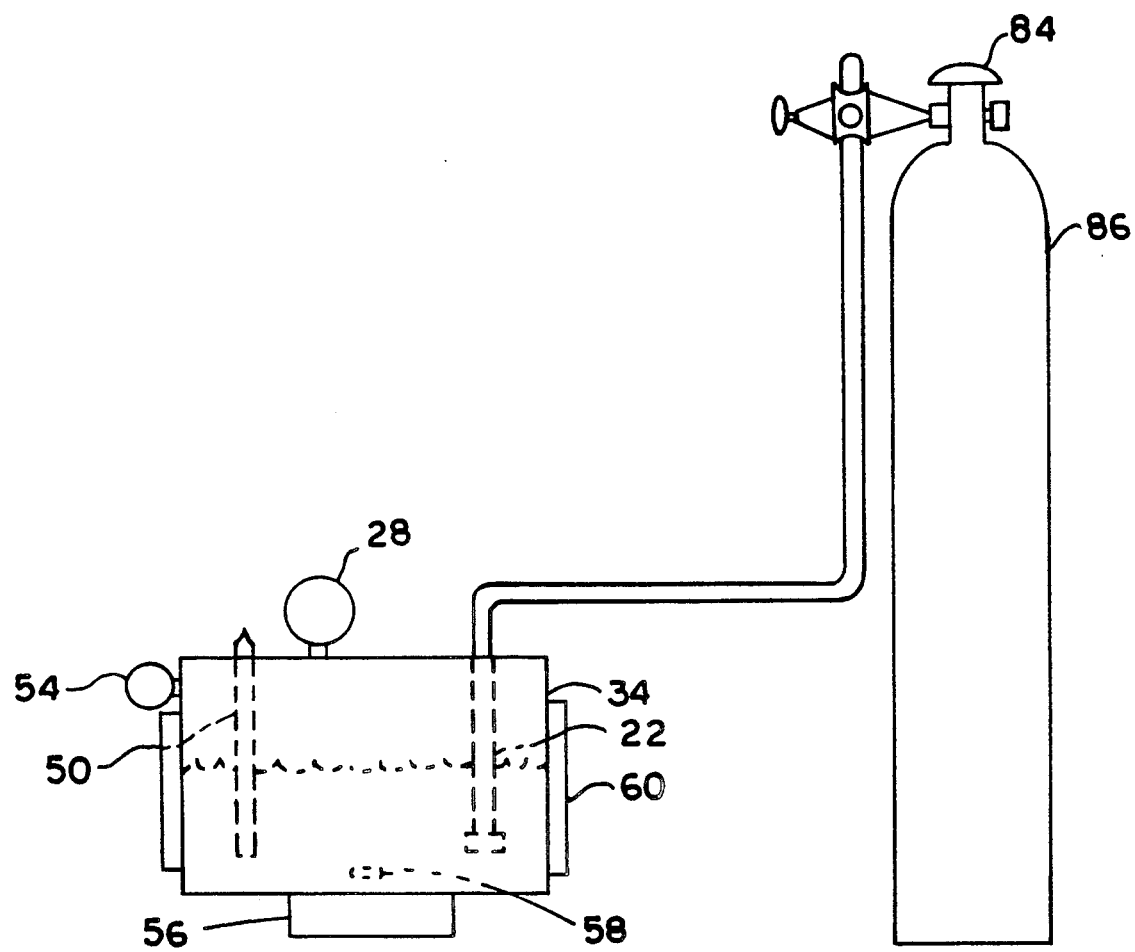
FIG. 6 shows the original working model of the gas liquid contact apparatus connected to a cylinder of oxygen gas.

Referring to FIG. 5, the glass syringe 78 containing the oxygenated liquid is packed in an ice slush and infused into a central venous catheter 94. The central venous catheter 94 connects to diffusion-resistant intravenous tubing 92 and a stopcock valve 90. A standard infusion pump 88 may be used to regulate the liquid flow rate into the patient's vein. When the oxygenated liquid containing a very high partial pressure is injected into the blood stream, which contains a low partial pressure, the dissolved oxygen in the liquid will diffuse into the surrounding blood resulting in an increase of the net oxygen concentration of the blood.

In order to achieve adequate oxygen delivery to tissues using the method of intravenously injecting oxygenated liquids, two variables may be manipulated. These variables are the (1) partial pressure of oxygen dissolved in the infused liquid (abbreviated as the $po_2$) and (2) the flow rate of fluid injection. The combination of these two variables will ultimately determine the net change in blood oxygen content and; subsequently, oxygen delivery to tissues. Following injection into the bloodstream, it is believed that the mixing of the oxygenated liquid with blood will result in significant increases in the partial pressure of oxygen dissolved in blood plasma which in turn will increase hemoglobin saturation with oxygen. The increases in both the dissolved $po_2$ and the oxyhemoglobin percent saturation raise the oxygen content of mixed venous blood, and; subsequently, the oxygen content of arterial blood is increased. Therefore, an overall net increase of oxygen delivery to tissues occurs. The variables of fluid infusion flow rate and the $po_2$ of the liquid may be manipulated to maintain a rate of oxygen delivery to tissues of 800.0 to 1000.0 milliliters of oxygen per minute.

The oxygenated liquid may be injected into the bloodstream as a continuous infusion or injected as a bolus during emergencies. During continuous infusions, fluid flow rate of 30.0 to 500.0 milliliters per hour may be used for adults. Because of the relatively small volume of liquid infused per minute during a continuous infusion, it is expected that the oxygenated liquid $po_2$ must be significantly increased (compared to the normal liquid $po_2$ of 159 mm Hg.) in order to appreciably increase the blood oxygen level. For example, at a continuous infusion rate of 100.0 milliliters per hour (0.027 ml. per second) it is expected that the liquid $po_2$ must be approximately 3040 mm Hg. in order to increase the mixed venous $po_2$ by a factor of about 2.0 mm Hg. per second. A continuous infusion of the oxygenated liquid may be beneficial when supplemental blood oxygenation is required to support moderate lung impairment from a disease like pneumonia. This type of supplemental oxygenation may be life-saving when lung impairment results in hypoxemia despite traditional treatment with oxygen inhalation.

The injection of a bolus solution refers to the relatively rapid infusion of a large volume of liquid in a short period of time. During a bolus injection, 50.0 to 200.0 milliliters of oxygenated liquid could be infused over a period of 10 minutes. The injection of a bolus of oxygenated liquid may be extremely useful in emergency situations like choking where the breathing passages are completely blocked and no oxygen exchange occurs in the lungs. Left untreated, tissue death will occur in minutes due to hypoxia. On the other hand, a bolus injection of oxygenated liquid containing a high $po_2$ provides immediate blood oxygenation which would otherwise be impossible until the breathing passages are cleared.

The optimal $po_2$ and infusion rate of the oxygenated liquid may vary from one patient to another because of individual differences in physiological function. However, the following physiologic factors must be considered when blood oxygen levels are titrated with oxygenated liquid infusions:

Cardiac Output
Oxygen Content of Mixed Venous Blood
Oxygen Content of Arterial Blood
Hemoglobin Concentration
Fluid Intake And Output
Oxygen Consumption
Hemoglobin Affinity for Oxygen (p50)
Fractional Inspired Oxygen Concentration (Fio2)
Matching of Ventilation and Perfusion
Interpulmonary Shunt
Electrolytes (Sodium, Potassium, Chloride)

The efficacy of titrating blood with oxygenated liquids may be determined by conventional monitoring techniques such as periodic blood gas analysis, oximetry, transcutaneous oxygen analysis, and florescent optode measurement of blood gases.

In addition to intravenous injection, oxygenated liquids may be used for alternative therapeutic purposes. These include (1) topical application of oxygenated liquids to the skin and body surfaces, (2) the injection of oxygenated liquids into body cavities, (3) the injection of oxygenated liquids for regional tissue oxygenation, and (4) the use of an oxygenated liquid as an antimicrobial agent.

Figure 7:
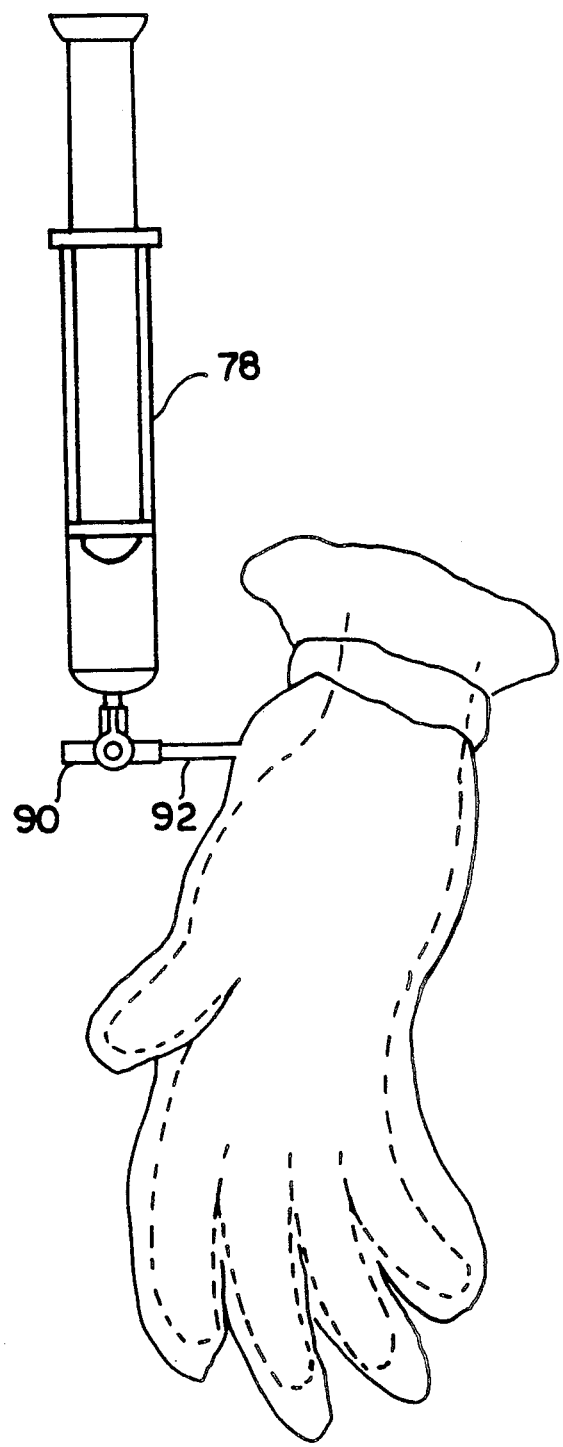
FIG. 7 shows the injection of the super-oxygenated liquid into a diffusion-resistant apparatus for topical application to the skin and body surfaces.

As shown in FIG. 7, the oxygenated liquid may be injected into a diffusion-resistant container in order to topically apply the oxygenated liquid to the skin and body surfaces. When the oxygenated liquid contacts the skin or body surface, the oxygen may be directly absorbed into the tissue and body fluids by means of diffusion. This type of application may be especially useful in the treatment of wounds which have a poor blood supply. The rationale for this form of therapy is based upon the fact that adequate tissue oxygenation is essential for normal healing to occur. Frequently, the local circulation of blood is disrupted when a wound occurs, thereby limiting the available oxygen delivered by the blood to injured tissue. Wounds deprived of oxygen heal very slowly or not at all. The critically low $po_2$ is thought to range from 7.0 to 20.0 mm Hg. for healing to occur. Oxygen is essential to healing in 3 ways: (1) the formation of granulation (scar) tissue consumes oxygen, (2) molecular oxygen is essential for the hydroxlyation of proline and lysine during collagen synthesis by fibroblast cells, and (3) an optimal tissue $po_2$ must be maintained for cellular proliferation of fibroblast cells which are essential for collagen synthesis and healing to occur. In essence, the topical application of oxygenated liquids allows adequate tissue oxygenation even when blood flow is disrupted. When adequate tissue oxygenation is maintained, both the rate and tensile strength of wound healing are increased.

Circumstances in which oxygenated liquids may be topically applied to accelerate wound healing include pressure sores on the skin, skin ulcers, burns, and wounds following surgery. In addition, the direct application of oxygenated liquids to the skin eliminates the problem of blood flow occlusion which occurs when gaseous oxygen is hyperbarically applied to the skin.

Figure 8:
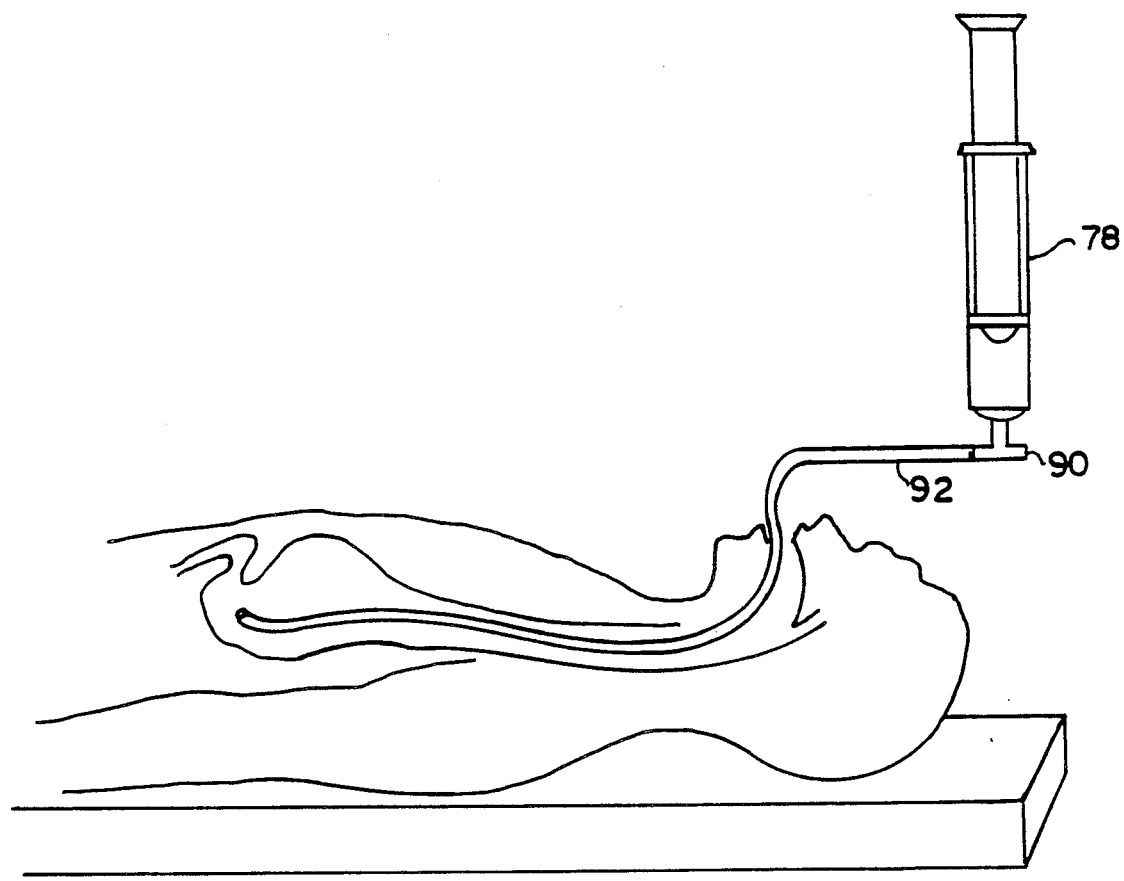
FIG. 8 shows the injection of the super-oxygenated liquid into the gastro-intestinal tract by means of a diffusion-resistant tube.

As shown in FIG. 8, the oxygenated liquid may be injected into body cavities such as the gastrointestinal tract for two purposes. First, body cavities with a highly vascular morphology may allow significant quantities of oxygen to be absorbed directly into the bloodstream. Second, oxygen has a vasoconstrictive chemical effect on blood vessels, which means that oxygen may be useful in controlling bleeding disorders in vascular tissue. A specific circumstance in which an oxygenated liquid may be especially useful when injected into the gastrointestinal tract is during the treatment of a bleeding stomach ulcer. The rationale for this method of treatment is that oxygen will chemically induce arterial blood vessels to constrict and decrease the bleeding. In addition, as previously described, adequate tissue oxygenation enhances both the rate and tensile strength of healed tissue in the healing process.

Figure 9:
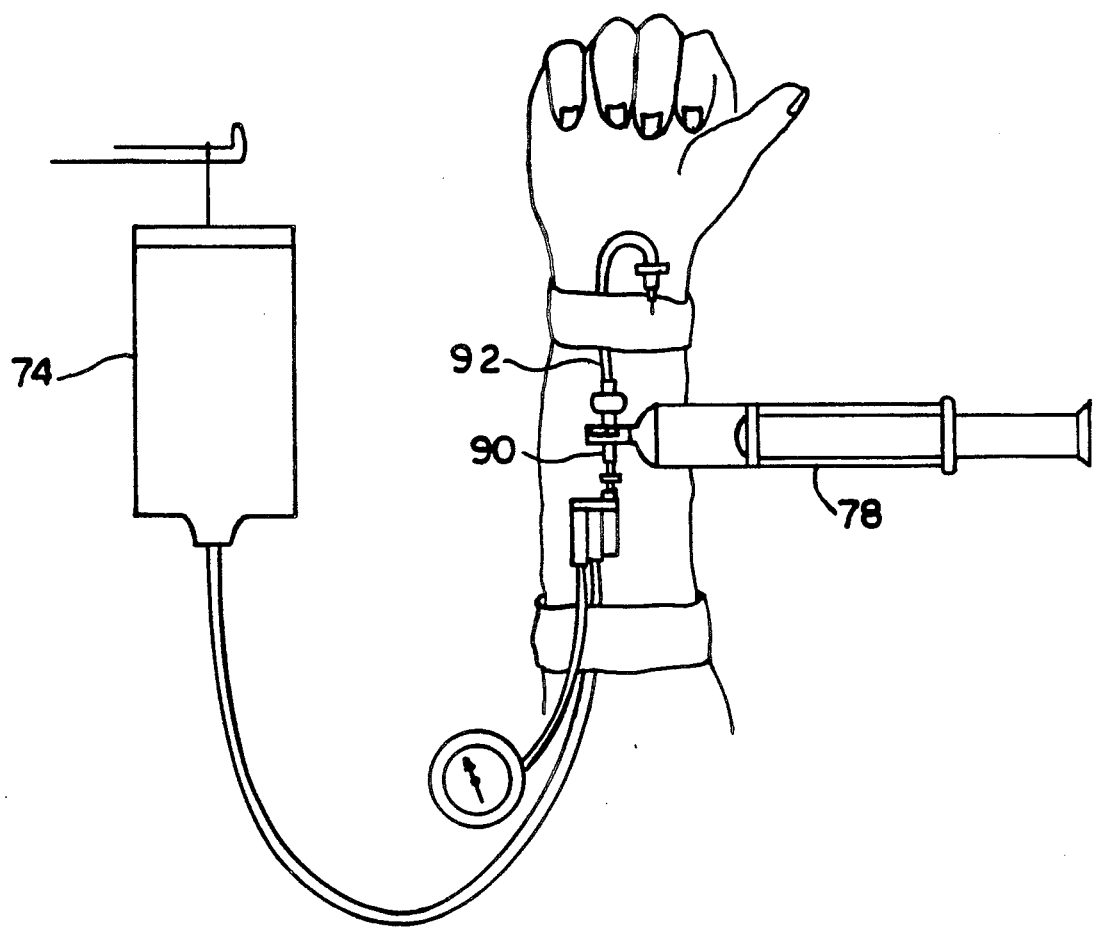
FIG. 9 shows the injection of the super-oxygenated liquid into an arterial blood vessel via an arterial catheter system for regional tissue hyper-oxygenation.

As shown in FIG. 9, the oxygenated liquid may be injected into an artery via a standard arterial catheter system in order to locally increase tissue oxygenation. A localized increase in tissue oxygenation is desirable in the treatment of certain cancerous tumors. The rationale for this form of treatment is that radiation therapy is enhanced when regional oxygenation of the cancerous tumor is increased. Also, the injection of an oxygenated liquid may be useful in improving regional tissue oxygenation when the liquid is injected "downstream" or distal to an occluded artery. Specific circumstances in which this method of using oxygenated liquids may be beneficial include the treatment of occluded coronary arteries during myocardial infarction and the treatment of occluded carotid arteries during a cerebrovascular accident (stroke). In both of these situations, regional tissue oxygenation may be improved while the cause of the blood vessel occlusion is corrected.

Another use of an oxygenated liquid is to kill microorganisms; especially those that are harmful and result in infection. The rationale for this use of an oxygenated liquid is twofold. First, molecular oxygen is an essential substrate for microbicidal killing mechanisms of phagocytic neutrophil cells. More specifically, adequate oxygenation is necessary for normal function of the pyridine nucleotide, NADPH oxidase system. In addition, adequate oxygenation of neutrophils ensures the production of hydrogen peroxide and superoxide anion within the phagocytic vacuoles of the neutrophil cells. Therefore, following ingestion of a harmful microbe by a neutrophil cell, oxygenated liquids may be used to provide a source of molecular oxygen to enhance the leukocyte's microbicidal systems.

Second, oxygenated liquids may be used to directly cause microbial death due to the effects of oxygen toxicity. Oxygen toxicity has been defined as any variation from the normal structure or function attributable to the action of oxygen which produces deleterious effects on cells. Oxygen is thought to be toxic to microbes, especially anaerobic organisms, because of the generation of free radicals such as the superoxide radical upon exposure to oxygen. The anti-microbial effects of superoxide depends upon the superoxide-degrading enzymes called superoxide dismutases. In general, aerobic organisms contain abundant superoxide dismutases and are somewhat insensitive to superoxide. However, strictly anaerobic microbes (those that live in the absence of oxygen) contain no superoxide dismutase, and may be killed by the superoxide anion. For example, a $po_2$ of about 1400 mm Hg. is thought to be bactericidal to the anaerobe, Clostridium perfringens. Therefore, oxygenated liquids may be used to kill a variety of susceptible microbes (including viruses, bacteria, fungi, and Mycoplasma organisms) due to induction of microbial oxygen toxicity. For use as an anti-microbial agent, the oxygenated liquid may be administered in any of the aforementioned manners including injection into the bloodstream, injection into body cavities, and topical application to infected skin or body surfaces.

While the above description contains many specificities, these should not be construed as limitations on the scope of the invention, but rather as an exemplification of one preferred embodiment thereof. Many other variations are possible, such as utilizing mechanisms such as bubbling the oxygen gas through the liquid inside the pressure vessel, aerosolization of the liquid inside the pressure vessel, or having the gas contact a thin film of liquid in the pressure vessel. In addition to intravenous injection, the oxygenated liquid may be topically applied to body surfaces and systemically injected for absorption into the bloodstream.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of oxygen therapy comprising:
   (a) oxygenating a non-blood liquid extracorporeally by contacting the liquid with oxygen under hyperbaric pressures;
   (b) maintaining the liquid in contact with oxygen until the partial pressure of oxygen in the liquid reaches at least 760 mm Hg.; and
   (c) treating a patient with the oxygenated liquid while maintaining the partial pressure of oxygen at hyperbaric pressures.

2. The method according to claim 1 wherein the liquid is contacted with oxygen under pressures of at least three atmospheres.

3. The method according to claim 2 wherein the liquid is maintained in contact with oxygen until the partial pressure of oxygen in the liquid reaches at least 2280 mm Hg.

4. The method according to claim 1 wherein the liquid is contacted with oxygen under pressures of at least 4 atmospheres.

5. The method according to claim 4 where the liquid is maintained in contact with oxygen until the partial pressure of oxygen in the liquid reaches at least 3040 mm Hg.

6. The method according to claim 1 wherein the step of oxygenating the liquid includes refrigerating the liquid to increase the solubility of oxygen.

7. The method according to claim 1 wherein the step of oxygenating the liquid includes stirring the liquid to enhance dissolution of oxygen into the liquid.

8. The method according to claim 7 wherein the step of oxygenating the liquid includes generating a magnetic field which passes through the liquid to improve the solubility of the oxygen into the liquid.

9. A method of oxygen therapy comprising:
   (a) placing a non-blood liquid in a contact apparatus;
   (b) contacting the liquid in the contact apparatus with oxygen or oxygen containing gas to effect dissolution of the oxygen into the liquid;
   (c) maintaining contact between the liquid and oxygen or oxygen containing gas until the partial pressure of oxygen in the liquid is greater than 760 mm Hg.;
   (d) transferring the oxygenated liquid to an infusion apparatus while maintaining a partial pressure greater than 760 mm Hg.; and
   (e) injecting the oxygenated liquid while maintaining a partial pressure of oxygen greater than 760 mg Hg. into a patient's bloodstream, thereby allowing the oxygen present in the oxygenated liquid to diffuse into the blood plasma.

10. The method according to claim 9 wherein the liquid is maintained in contact with oxygen or oxygen containing gas until the partial pressure of oxygen in the liquid is greater than 760 mm Hg.

11. The method according to claim 9 wherein the liquid is contacted with oxygen under pressures greater than 1 atmosphere.

12. The method according to claim 9 wherein the liquid is contacted with oxygen or oxygen containing gas under pressures of at least 3 atmospheres.

13. The method according to claim 12 wherein the liquid is maintained in contact with oxygen until the partial pressure of oxygen in the liquid is greater than 2,280 mm Hg.

14. The method according to claim 9 wherein the liquid is contacted with oxygen or oxygen containing gas under pressures of at least 4 atmospheres.

15. The method according to claim 14 wherein the liquid is maintained in contact with oxygen or oxygen containing gas until the partial pressure of oxygen in the liquid is at least 3,040 mm Hg.

16. The method according to claim 9 wherein the step of contacting the liquid with oxygen or oxygen containing gas includes refrigerating the liquid to increase the solubility of the oxygen.

17. The method according to claim 9 wherein the step of oxygenating the liquid includes generating a magnetic field which passes through the liquid to improve the solubility of the oxygen into the liquid.

18. A method of oxygen therapy comprising:
(a) introducing a liquid into a contact apparatus;
(b) oxygenating the liquid by contacting the liquid in the contact apparatus with oxygen or oxygen containing gas under hyperbaric pressures thereby effecting dissolution of oxygen into the liquid;
(c) pressurizing the contents of the contact apparatus;
(d) drawing the oxygenated liquid from the contact apparatus into a diffusion resistant treatment apparatus; and
(e) treating a patient with the oxygenated liquid while maintaining the partial pressure of oxygen at hyperbaric pressures to cause absorption of the dissolved oxygen in the liquid into body fluids and tissues.

19. The method according to claim 18 wherein the step of treating a patient comprises injecting the oxygenated liquid intravenously into the patient's bloodstream when lung impairment exists in sufficient quantity to effect an increase in the oxygen content of the blood.

20. The method according to claim 19 wherein the liquid is injected intravenously in sufficient quantity to maintain the partial pressure of oxygen in the arterial blood at about 100 mm Hg.

21. The method according to claim 19 wherein the liquid is injected intravenously in sufficient quantity to maintain percent of hemoglobin saturation with oxygen in arterial blood at about 95 percent.

22. The method according to claim 19 wherein the liquid is injected intravenously in sufficient quantity to maintain the oxygen content of arterial blood at about 20 volume percent.

23. The method according to claim 19 wherein the liquid is injected in sufficient quantity to maintain the rate of oxygen delivery to tissues at about 800–1000 ml per minute.

* * * * *